US012667492B2

(12) United States Patent
Vaughan et al.

(10) Patent No.: US 12,667,492 B2
(45) Date of Patent: ***Jun. 30, 2026

(54) TYMPANOSTOMY TUBE AND PLACEMENT DEVICE

(71) Applicant: AVENTAMED DESIGNATED ACTIVITY COMPANY, Cork (IE)

(72) Inventors: John Vaughan, Cork (IE); Olive O'Driscoll, Kinsale (IE); Carol Grimes, Skerries (IE)

(73) Assignee: KARL STORZ SE & Co. KG, Tuttlingen (DE)

( * ) Notice: Subject to any disclaimer, the term of this patent is extended or adjusted under 35 U.S.C. 154(b) by 93 days.

This patent is subject to a terminal disclaimer.

(21) Appl. No.: 18/070,911

(22) Filed: Nov. 29, 2022

(65) Prior Publication Data

US 2023/0110173 A1 Apr. 13, 2023

Related U.S. Application Data

(63) Continuation of application No. 16/331,487, filed as application No. PCT/EP2017/072461 on Sep. 7, 2017, now Pat. No. 11,547,609.

(30) Foreign Application Priority Data

Sep. 8, 2016 (EP) ..................................... 16187871

(51) Int. Cl.
*A61F 11/20* (2022.01)
*A61B 17/34* (2006.01)

(52) U.S. Cl.
CPC ........ *A61F 11/202* (2022.01); *A61B 17/3415* (2013.01); *A61B 17/3468* (2013.01)

(58) Field of Classification Search
CPC ............... A61F 11/202; A61B 17/3415; A61B 17/3468
See application file for complete search history.

(56) References Cited

U.S. PATENT DOCUMENTS

| | | | |
|---|---|---|---|
| 5,976,151 A | 11/1999 | Siegbahn | |
| 2008/0262510 A1* | 10/2008 | Clifford .................. | A61N 1/306 604/501 |

(Continued)

FOREIGN PATENT DOCUMENTS

| | | |
|---|---|---|
| CA | 2 643 179 A1 | 5/2010 |
| WO | 2011/008948 A1 | 1/2011 |

(Continued)

OTHER PUBLICATIONS

International Search Report issued in PCT/EP2017/072461; mailed Jan. 24, 2018.

*Primary Examiner* — Rebecca E Eisenberg
*Assistant Examiner* — Matthew Wrubleski
(74) *Attorney, Agent, or Firm* — David N. Villalpando; Jason Worgull; Jacqueline Cohen

(57) ABSTRACT

A tympanostomy tube placement device has a needle with a tip, and a retainer at the needle tip. The retainer is within and retains by pulling radially inwardly a tympanostomy tube distal flange in a folded configuration extending distally. Movement of the needle tip in the proximal direction causes the adhesive bond to break and the distal flange releases to an unconstrained deployed position. Due to the axial folding of the distal flange its radial dimension does not affect deployment through the membrane.

18 Claims, 9 Drawing Sheets

(56)         References Cited

U.S. PATENT DOCUMENTS

| | | | |
|---|---|---|---|
| 2009/0209972 A1* | 8/2009 | Loushin | A61M 31/00 |
| | | | 606/109 |
| 2014/0276928 A1 | 9/2014 | Vanderpool et al. | |
| 2015/0164695 A1* | 6/2015 | Liu | A61B 17/3478 |
| | | | 606/109 |
| 2016/0045369 A1* | 2/2016 | Clopp | A61F 11/202 |
| | | | 606/109 |
| 2016/0045371 A1 | 2/2016 | Girotra et al. | |
| 2017/0014272 A1* | 1/2017 | Ray | A61F 11/202 |
| 2019/0192349 A1* | 6/2019 | Vaughan | A61F 11/202 |
| 2019/0321610 A1* | 10/2019 | Goldfarb | A61M 31/002 |
| 2021/0169697 A1* | 6/2021 | Vaughan | A61B 17/3468 |

FOREIGN PATENT DOCUMENTS

| | | | | |
|---|---|---|---|---|
| WO | WO-2013188338 A1 * | 12/2013 | | A61B 17/3468 |
| WO | WO-2014075949 A1 * | 5/2014 | | A61F 11/002 |
| WO | WO-2016022899 A1 * | 2/2016 | | A61B 17/3468 |
| WO | 2016099670 A1 | 6/2016 | | |

* cited by examiner

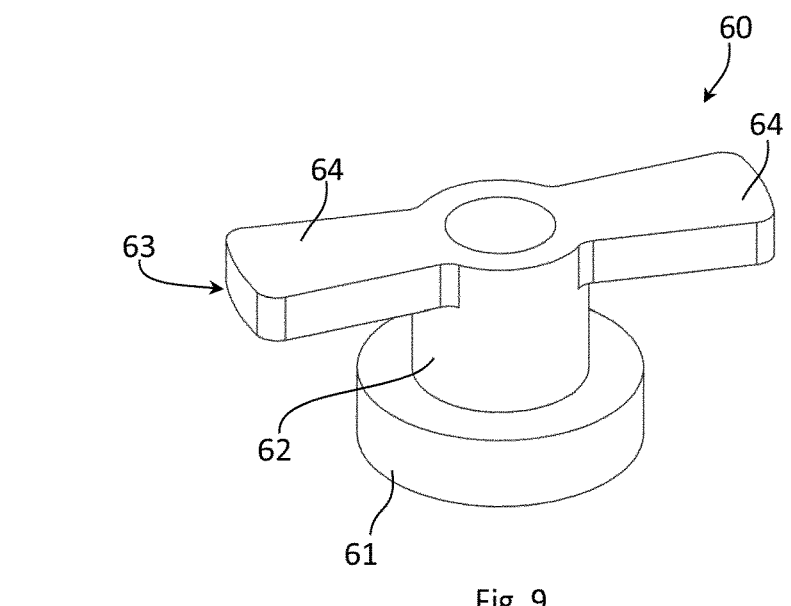
Fig. 9
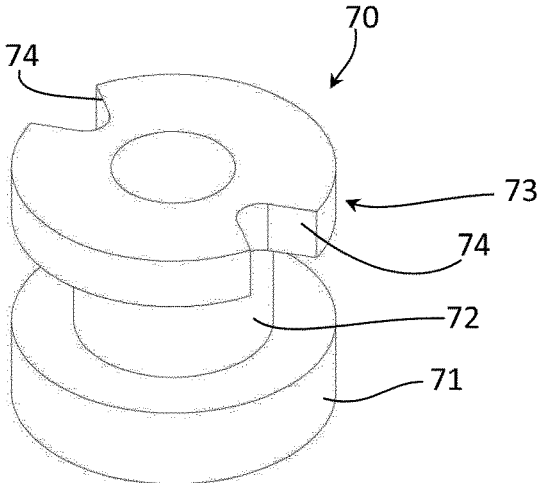
Fig. 10
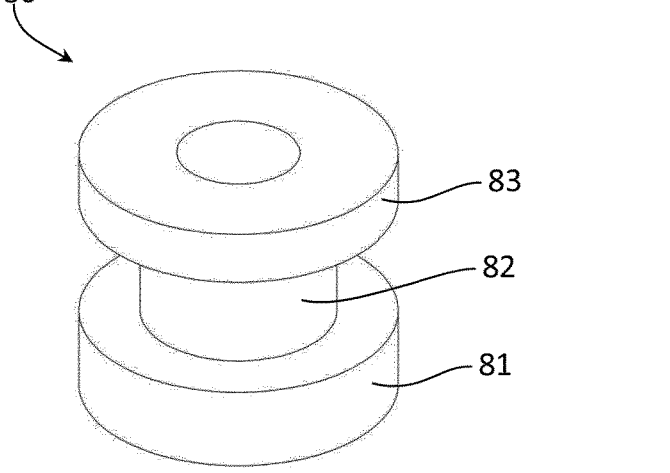
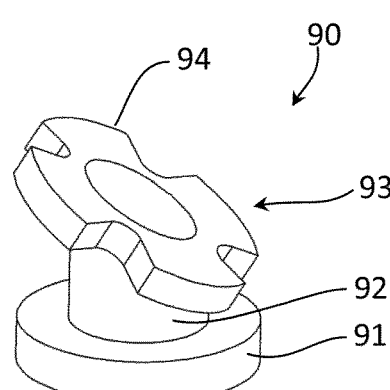
Fig. 11                                              Fig. 12

TYMPANOSTOMY TUBE AND PLACEMENT DEVICE

INTRODUCTION

Field of the Invention

The invention relates to tympanostomy tubes and applicators or "placement devices" for deploying them.

Prior Art Discussion

A tympanostomy tube applicator is a minimally-invasive tool that aids physicians in treating patients suffering from ear conditions for example Otitis Media, who require tympanostomy tube placement. The condition is treated by inserting a tympanostomy tube across the tympanic membrane (or, "ear drum") to ventilate the middle ear space and equalize the pressure between the middle and outer ear. Tympanostomy tube insertion is the main reason why children undergo surgery with a general anaesthetic. An applicator allows tympanostomy tubes to be placed safety and quickly in patients tympanic membrane.

WO2014/075949 (Cork Institute of Technology) and WO2011/008948 (Acclarent) describe such applicators. In these devices the tip creates an incision in the tympanic membrane and ejects a tympanostomy tube into the membrane. The tube in WO2014/075949 is restrained by sleeves surrounding it and a knife pulls through to deploy the tube. WO2011/008948 (Acclarent) describes a tube delivery system in which a tympanostomy tube is restrained by sleeves surrounding it so that its flanges lie axially.

The invention is directed towards providing an applicator for effective deployment of a tube; and another object is to allow placement of tubes with good versatility in choice of size of distal flange to provide a wide range of dwell times.

SUMMARY OF THE INVENTION

We describe a tympanostomy tube applicator comprising a needle with a tip and a stem, and a retainer on the needle stem. The retainer is configured to fit within and retain a tympanostomy tube distal flange in a folded configuration having a direction with a primarily axial component such that movement of the needle tip causes the distal flange to release from the retainer to a deployed position having a direction with a primarily radial component.

The term "applicator" is used in this document, and this is equivalent to the term "placement device", its purpose being to allow a surgeon to place the tube in the membrane.

Preferably, the needle is arranged to move axially to cause release of the tube distal flange from the retainer.

Preferably, the retainer comprises recesses for retaining wings of a winged tube distal flange. This is an effective way of allowing the retainer to, pre-deployment, pull the flange wings into the axial or near-axial position, from within.

The applicator may comprise a stop surface to stop axial movement of a tube proximal flange, such that the retainer squeezes the tube against the stop surface to cause the distal flange to release during axial movement of the needle in the proximal direction. The stop surface may be on a sleeve into which the needle is inserted.

The retainer may include a discrete component on the needle. The retainer discrete component may be of plastics material.

Preferably, the retainer discrete component has a through-hole through which the needle stem extends, and the component is in contact with the needle tip.

Preferably, the retainer is arranged to retain the distal flange in the pre-deployment folded configuration by at least adhesive.

The retainer may be arranged to retain the distal flange in the pre-deployment folded configuration by at least mechanical engagement. The retainer may comprise fingers engaging eyelets on the tube distal flange.

The retainer may comprise dovetail or slot features for engagement with a tube distal flange.

The retainer may be adapted to engage with a tube by welding or magnetism for retaining the distal flange in the folded configuration.

The applicator may further comprise a tympanostomy tube having a proximal flange, a bridge with a lumen, and a distal flange, in which said tube is mounted on the needle with the needle stem extending through the lumen and with said distal flange folded and retained in said folded position by the retainer. It is advantageous that the applicator is pre-loaded with a tube ready for deployment The applicator may be a cartridge for attachment to a handle with a mechanism for movement of said needle.

The applicator may further comprise an integral handle with a mechanism for movement of the needle.

We also describe a tympanostomy tube comprising a proximal flange, a bridge, a distal flange, and a lumen, wherein the distal flange is configured to be retained at a folded orientation with a direction having a primarily axial component and to release to a deployed position having a direction with a primarily radial component upon movement of a retainer located radially within the distal flange.

Preferably, the distal flange comprises a plurality of wings.

The distal flange may be configured to have an angle to axial in the folded position in the range of 0° to +/−20°.

Preferably, the distal flange is configured to have an angle to axial in the unconstrained deployed position in the range of 400 to 140°.

The bridge may be of a material which is resilient to allow a needle tip of larger diameter than the lumen to pass through.

The distal flange may have two wings or three wings or four wings for example.

The distal flange may be annular-shape, optionally with radial cut-outs.

The distal flange may comprise at least one mechanical engagement part arranged to engage mechanically a needle retainer, and each mechanical engagement part may be an eyelet for receiving a retainer part or a tab for engagement behind or within a slot or eyelet of the retainer.

The distal flange may include an insert of a material which is different from surrounding material, said insert being configured for attachment to a retainer by, for example, welding, magnetism, or adhesive.

We also describe a method of deploying a tympanostomy tube across a tympanic membrane, in which:

the tube comprises a proximal flange, a bridge, a distal flange, and a lumen, the method is performed with an applicator comprising a needle with a stem and a tip, and a retainer on the needle stem the tube is mounted on the retainer with the needle stem through the tube lumen, and the tube distal flange is retained in a folded position to have a primarily axial component facing distally; the method comprising the steps of:

piercing the tympanic membrane with the needle tip and locating the needle so that the tube distal flange is distal of the membrane and the tube bridge passes through the membrane, moving the retainer relative to the tube to cause separation of the tube distal flange from the retainer, freeing the distal flange to spring out on a radial orientation unconstrained.

Preferably, the needle is moved axially to release the distal flange. Preferably, the needle movement is in the proximal direction.

The tube distal flange may be adhered to or mechanically engaged with a retainer on the needle.

The needle movement may be rotational in addition to or instead of being axial.

The tube distal flange may be retained at least by adhesive and an adhesive bond is broken during needle withdrawal.

The tube distal flange may be retained at least by mechanical engagement.

The tube distal flange may include parts which mechanically engage the retainer and/or the needle and are sheared upon retraction of the needle, and said parts may include eyelets.

The tube distal flange may be retained at least by welding.

The tube distal flange may be retained at least by magnetism.

Additional Statements

According to the invention there is provided a tympanostomy tube applicator comprising:

a needle with a tip, and a retainer at the needle tip for retaining a tympanostomy tube distal flange in a folded configuration with a direction having a primarily axial component such that movement of the needle tip causes the distal flange to release to a deployed position having a direction with a primarily radial component.

In one embodiment, the needle is arranged to move axially to cause separation of the tube distal flange from the retainer.

In one embodiment, the retainer comprises recesses for retaining wings of a winged tube distal flange. In one embodiment, the retainer is configured to adhere or lock to the distal flange up to a threshold axial force during withdrawal of the needle. Preferably, the applicator comprises a stop surface to stop axial movement of a tube proximal flange, the retainer squeezing the tube against the stop surface to cause the distal flange to release. In one embodiment, the stop surface is on the sleeve into which the needle is inserted.

In one embodiment, the retainer includes a discrete component on the needle. In one embodiment, the discrete component is of plastics material.

In one embodiment, the component has a through-hole through which a needle stem extends, and the component is in contact with the needle tip.

In one embodiment, the retainer is arranged to retain the distal flange in the pre-deployment folded configuration by at least adhesive.

In one embodiment, the retainer is arranged to retain the distal flange in the pre-deployment folded configuration by at least mechanical engagement.

In one embodiment, the retainer comprises fingers engaging eyelets on the tube distal flange. In one embodiment, the retainer comprises dovetail or slot features for engagement with a tube distal flange.

In one embodiment, the retainer is adapted to engage with a tube by welding or magnetism for retaining the distal flange in the folded configuration.

In one embodiment, the applicator further comprises a tympanostomy tube having a proximal flange, a shank, and a distal flange, in which said tube is mounted on the needle with said distal flange folded and retained in said folded position by the retainer.

In one embodiment, the applicator is a cartridge for attachment to a handle with a mechanism for movement of said needle.

In one embodiment, the applicator further comprises an integral handle with a mechanism for movement of the needle.

In another aspect, the invention provides a tympanic tube comprising a proximal flange, a bridge, a distal flange, and a lumen, wherein the distal flange is configured to be retained at a folded orientation with a direction having a primarily axial component and to release to a deployed position having a direction with a primarily radial component upon movement of the needle.

In one embodiment, the distal flange comprises a plurality of wings. In one embodiment, the distal flange has an angle to axial in the folded position in the range of 0° to +/−20°.

In one embodiment, the distal flange has an angle to axial in the unconstrained deployed position in the range of 400 to 140°. In one embodiment, the bridge is of a material which is resilient to allow a needle tip of larger diameter than the lumen to pass through.

In one embodiment, the distal flange has two wings. In one embodiment, the distal flange has three wings. In one embodiment, the distal flange has four wings.

In one embodiment, the distal flange is annular-shaped, optionally with radial cut-outs.

In one embodiment, the distal flange comprises at least one mechanical engagement part arranged to engage mechanically a needle retainer, and each mechanical engagement part may be an eyelet for receiving a retainer part or a tab for engagement behind or within a slot or eyelet of the retainer.

In one embodiment, the distal flange includes an insert of a material which is different from surrounding material, said insert being configured for attachment to a retainer by, for example, welding, magnetism, or adhesive.

In another aspect, the invention provides a method of deploying a tympanostomy tube across a tympanic membrane, in which:

the tube comprises a proximal flange, a bridge, a distal flange, and a lumen, the method is performed with an applicator comprising a needle with a stem and a tip, and the needle being movable, the tube is mounted on the needle with the needle stem through the tube lumen, and the tube distal flange is retained in a folded position to have a primarily axial component facing distally;

the method comprising the steps of:

piercing the tympanic membrane with the needle tip and locating the needle so that the tube distal flange is distal of the membrane and the tube bridge passes through the membrane,

moving the needle relative to the tube to cause separation of the tube distal flange from the needle, freeing the distal flange to spring out on a radial orientation unconstrained.

In one embodiment, the needle is moved axially to release the distal flange. In one embodiment, the needle movement is in the proximal direction.

In one embodiment, the tube distal flange is adhered to or mechanically engaged with a retainer on the needle.

In one embodiment, the needle movement is rotational.

In one embodiment, the tube distal flange is retained by one or more of an adhesive, mechanical engagement, welding, and magnetism.

DETAILED DESCRIPTION OF THE INVENTION

Brief Description of the Drawings

The invention will be more clearly understood from the following description of some embodiments thereof, given by way of example only with reference to the accompanying drawings in which:—

FIGS. 8 to 12 are perspective views of alternative tubes which could be deployed using applicators of various embodiments, the tubes being shown in their deployed configurations;

Figure 24:
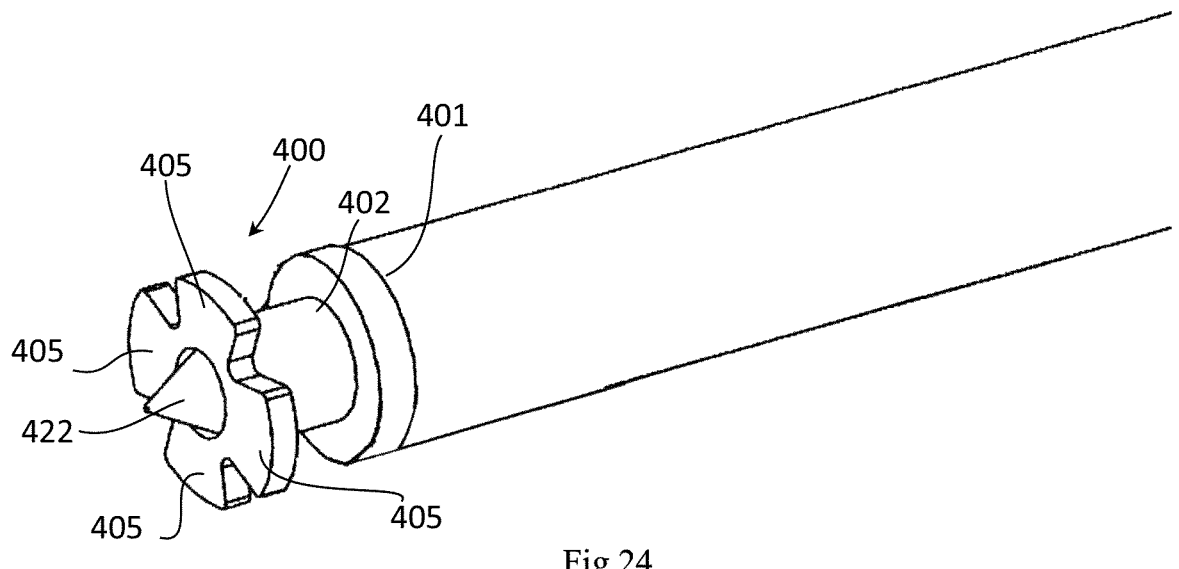

6 deployment, and FIG. 24 is a perspective view showing the tube after deployment as the applicator's needle is withdrawn.

DESCRIPTION OF THE EMBODIMENTS

Figure 1:
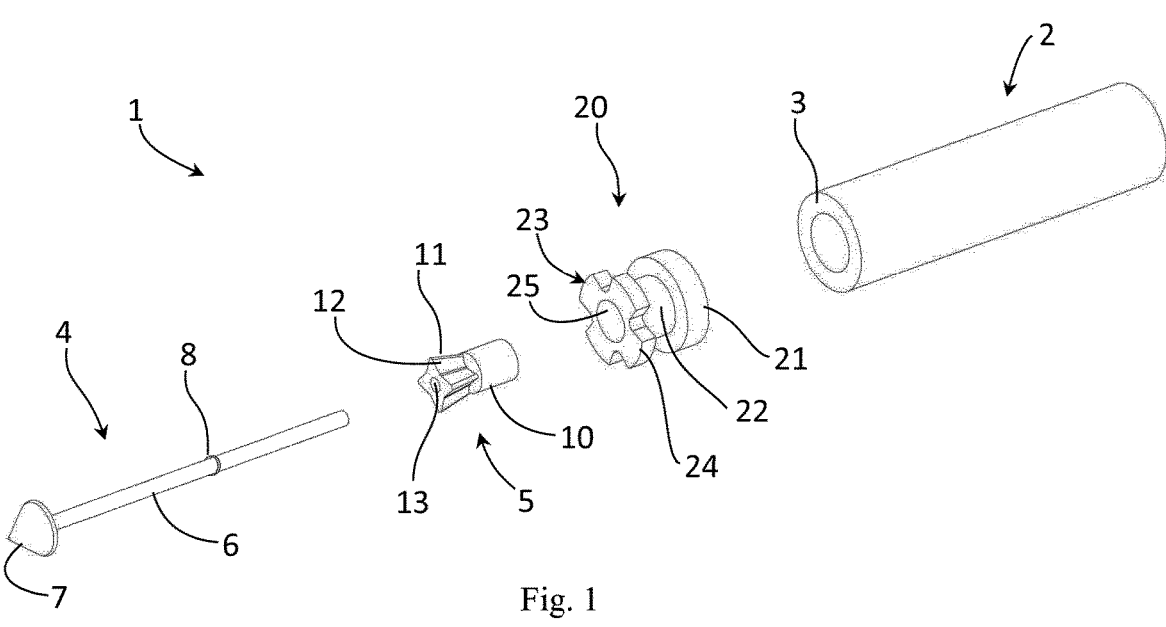
FIG. 1 is an exploded perspective view of the distal end of a tympanostomy tube applicator of the invention together with a tube in its deployed configuration.

Referring to FIG. 1 a tympanostomy tube applicator or placement device is for connection to a handle with a needle pull-through mechanism to pull a needle proximally in an action with a desired force could be used.

The placement device comprises a single-use cartridge replaceably connected to such a handle, and the cartridge has a distal end as shown in FIG. 1. The cartridge comprises a stem 2 with a distal end 3 to abut the proximal flange of a tympanostomy tube 20 to be deployed. The placement device is provided as a component to fit onto any desired mechanism to pull a needle axially, preferably spring-operated. For example, the handle may have a manually-operated latch which releases a spring to allow withdrawal of the needle under spring force. Such types of mechanisms are well known, even for household items such as writing pens.

A pull-through needle comprises a needle stem 6, a distal tip 7 of conical shape, and a moulded plastics tube retainer 5 held in place on the stem by a small flange 8 on the stem. The retainer may in other embodiments be of metal, and indeed may be integral with the stem. The retainer 5 is snap-fitted distally of the flange 8 and against the tip 7. The retainer 5 comprises a cylindrical base 10 and a tapered distal portion 11 with slots 12 to receive and retain folded wings 23 of a distal flange of the tube 20 when the retainer is within the distal end of the tube 20. Referring particularly to FIG. 1 the tube 20 comprises:

- a proximal flange 21 shaped to abut the distal end 3 of the stem 2,
- a central shank or bridge 22,
- a distal flange 23 comprising four orthogonally-arranged wings 24, and
- a lumen 25.

The view of the tube 20 is its post-deployment configuration. Pre-deployment, the distal flange 23 is folded to lie axially as shown in FIG. 2.

The lumen 25 extends through the tube 20, with a cross-sectional area suited to the intended use of balancing pressure across the tympanic membrane of the specified patient age group.

Figure 2A:
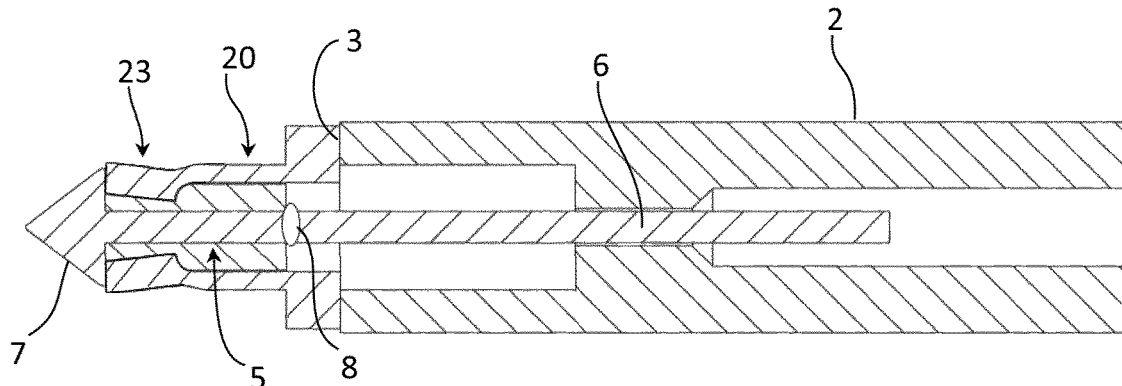
FIGS. 2(a), 2(b) and 3 to 6 are diagrams illustrating a sequence of steps for deployment of the tube using the applicator from a position at which the inner flange is near axial to radial as shown in FIG. 1.
Figure 2B:
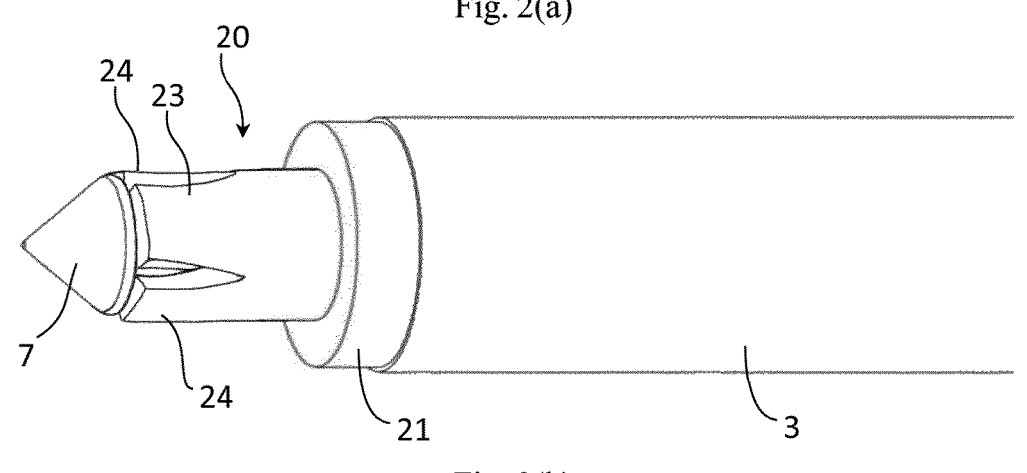

FIGS. 2(a) and 2(b) show the tube 20 before deployment, with the wings 23 folded to lie within, and adhered to, the recesses 12 of the retainer 5. At this position the wings 23 have a small angle to axial of about 0° to +/−20°, and the retainer is radially within the distal flange.

The tube wings 24 are of a more pliable material than the shank 22 and the proximal flange 21. This is achieved by co-moulding in an over-moulding process whereby the shank 22 can be made of a more rigid material than the wings 24.

After moulding of the tube 20 the manufacturer completes the cartridge by adhering the wings 24 into the recesses 12 using a suitable approved adhesive for medically invasive use. The wings 24 are therefore pulled from within into the axial orientation. The combined retainer 5 and tube 20 are slid along the needle stem 6, which is then inserted into the cartridge stem 2 lumen. This operation is complete when the needle's proximal end is in position to engage a handle drive mechanism, and the tube proximal flange 21 is against the face 3. The retainer 5 is snap-fitted onto the needle stem 6 as described above.

Figure 3:
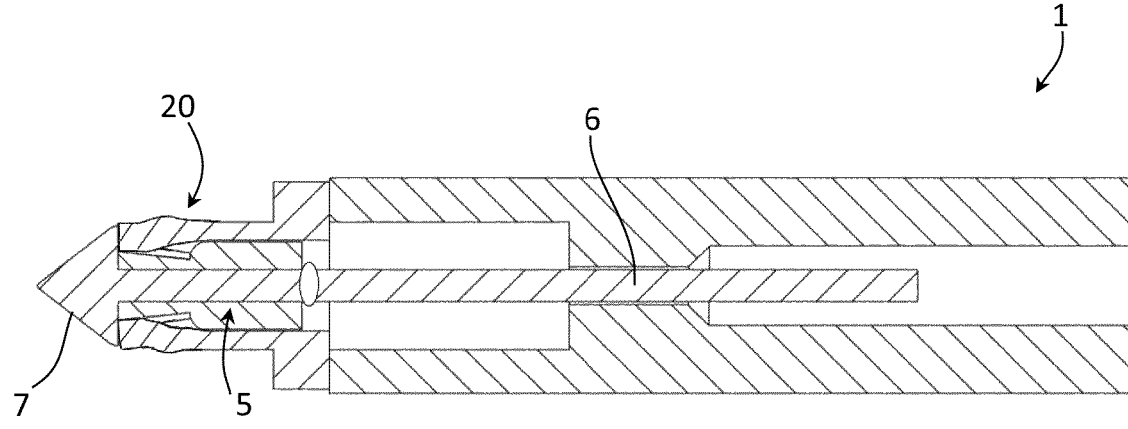
Figure 4:
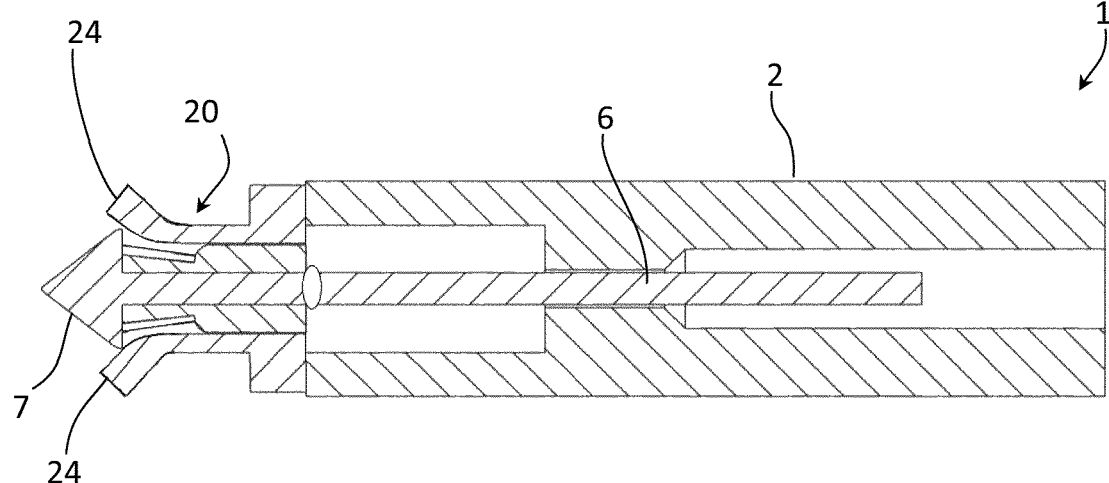
Figure 5:
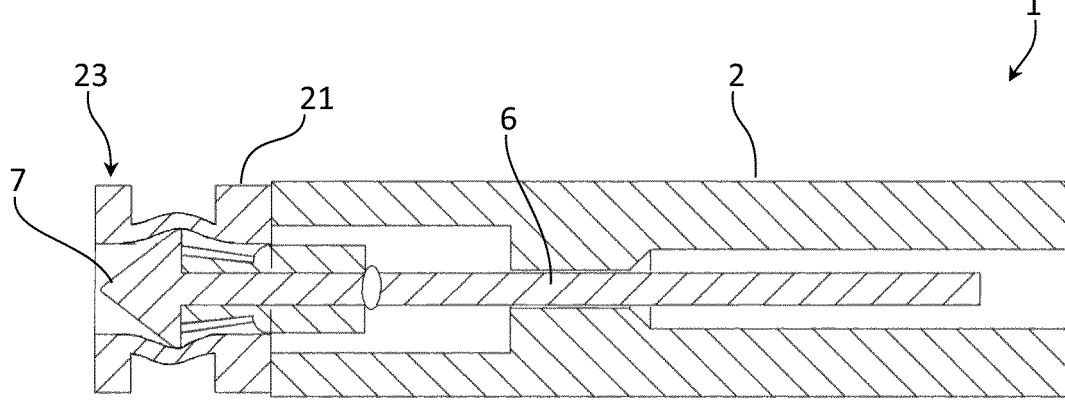
Figure 6:
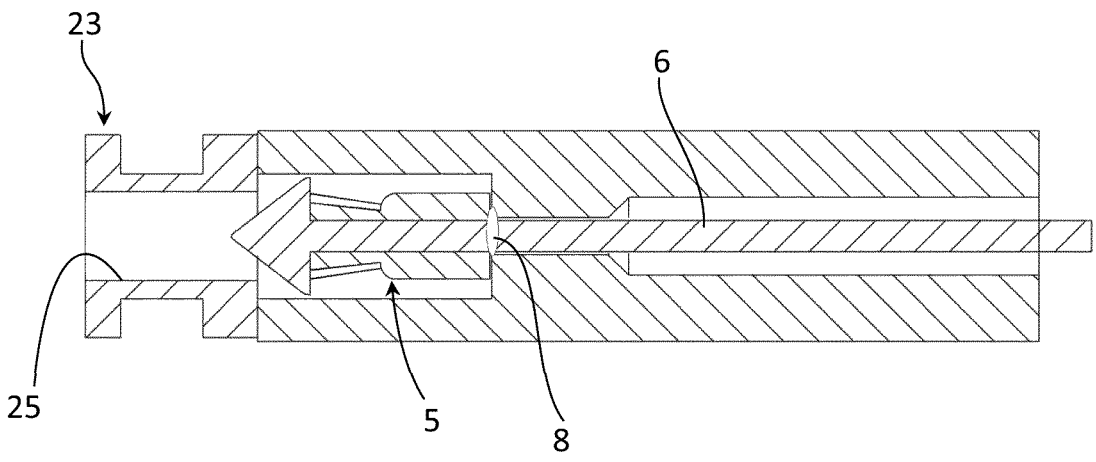

Deployment requires the surgeon to cause the needle tip 7 to pierce the tympanic membrane and move it until the distal flange wings 24 are at the inner (distal) side of the membrane. The handle drive mechanism is activated to pull the needle 4 through, causing (FIG. 3) the wings 24 to buckle until the adhesive breaks. This releases the pulling action of the needle's retainer on the wings, and so they are released to spring to the radial position (FIG. 4). The needle is then fully withdrawn (FIGS. 5 and 6).

This leaves the tube 20 in situ bridging the patient's tympanic membrane. It is noted that the tube shank or bridge 22 needs to deform because the tip 7 is wider than the lumen 24. So, while the shank 22 needs to be of a more rigid material than the distal flange 23, it does need sufficient resilience for this pull-through action. In order for the tube material not to cause too much force on the system so that the needle can successfully retract and release the tube distal flange, the material in the lumen needs to be flexible enough so that it does not increase the force on the needle retracting but is rigid enough to still hold its shape while implanted in the membrane.

In other embodiments the needle tip fits within the lumen of the tube, and so distortion of the tube's bridge is not required.

In this case the distal flange 23 use position is about 900 to axial, however it may more generally be in the range of 40° to 140° (see FIG. 12 for example), depending on the application.

It will be appreciated that the applicator allows very simple and effective tube deployment, while the distal flange is wide enough for a long dwell time of 15 to 24 months for example.

Figure 7:
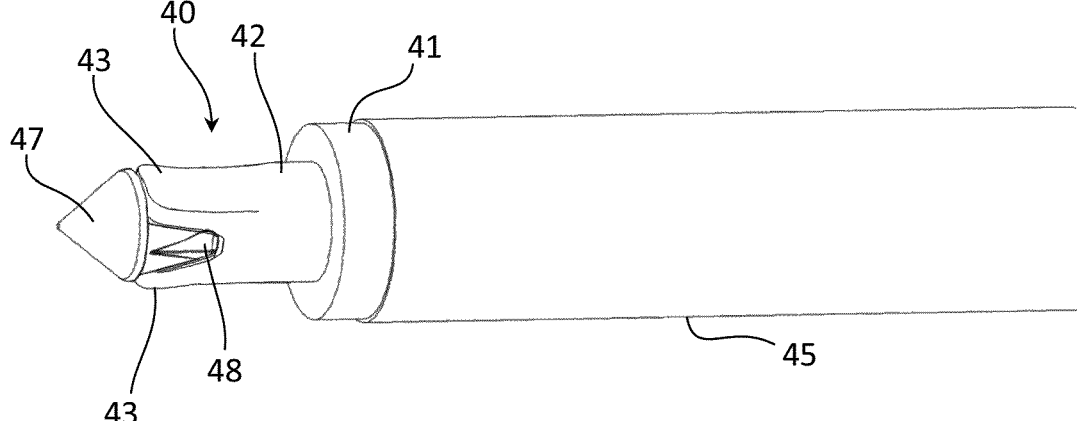
FIG. 7 is a perspective view of the distal end of an alternative applicator, in which a tube has an inner or "distal" flange with two wings.

FIG. 7 shows an applicator with a stem 45, a needle 47 and a retainer 48. In this case a tube 40 has a proximal flange 41, a shank 42, and a distal flange formed by two diametrically opposed wings 43 pulled radially inwardly by being adhered to sockets of the retainer 48.

Figure 8:
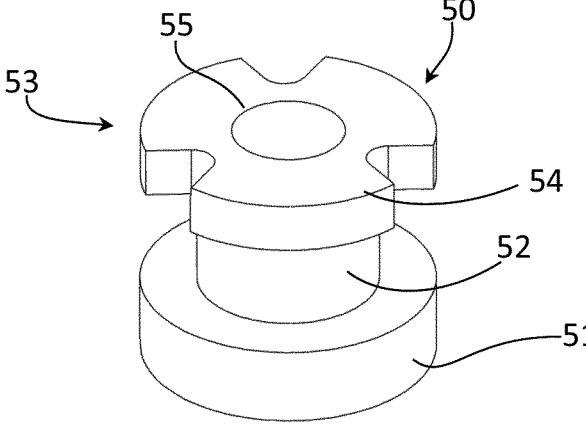

In other embodiments the tube has a different number of wings. FIG. 8 illustrates a tube 50 with a proximal flange 51, a shank 52, and a distal flange 53 with three wings 54 equi-spaced around a lumen 55. The applicator has a retainer configured with slots to adhere to the three wings.

FIG. 9 shows a tube 60 having a proximal flange 61, a shank 62, and a distal flange 63 having two diametrically opposed wings 64. This arrangement is known generally as a "T-tube", being particularly suitable for long dwell times, greater than 18 months, due to the length of the wings. In this embodiment the tube 60 has the overall configuration and use characteristic of such a T-tube, but the distal flange materials are suitable for lying axially while adhered to the applicator tip before deployment.

It will be appreciated that the placement device, by pulling the distal flange into axial alignment pre-deployment, allows independence of distal flange diameter from deployment considerations. This allows excellent versatility.

FIG. 10 shows a tube 70 having a proximal flange 71, a shank 72, and a distal flange 73 which is disc-shaped with two opposed notches 74 to provide flexibility for deployment. If the distal flange material is more flexible, it may be completely ring-shaped, without notches which are to aid folding onto the insert.

FIG. 11 shows such a tube 80, having a proximal flange 81, a shank 82, and a distal flange 83. In this case the distal flange 80 is fully annular in shape, the pre-deployment folding being achieved entirely due to flexibility of the flange material.

FIG. 12 shows a tube 90 with a proximal flange 91, a shank 92, and a distal flange 93 in a bevelled configuration at an acute angle to axial. There are four wings 94. This tube is suitable for long stay times. The bevelled configuration can aid folding the inner flanges onto the insert.

Figure 13:
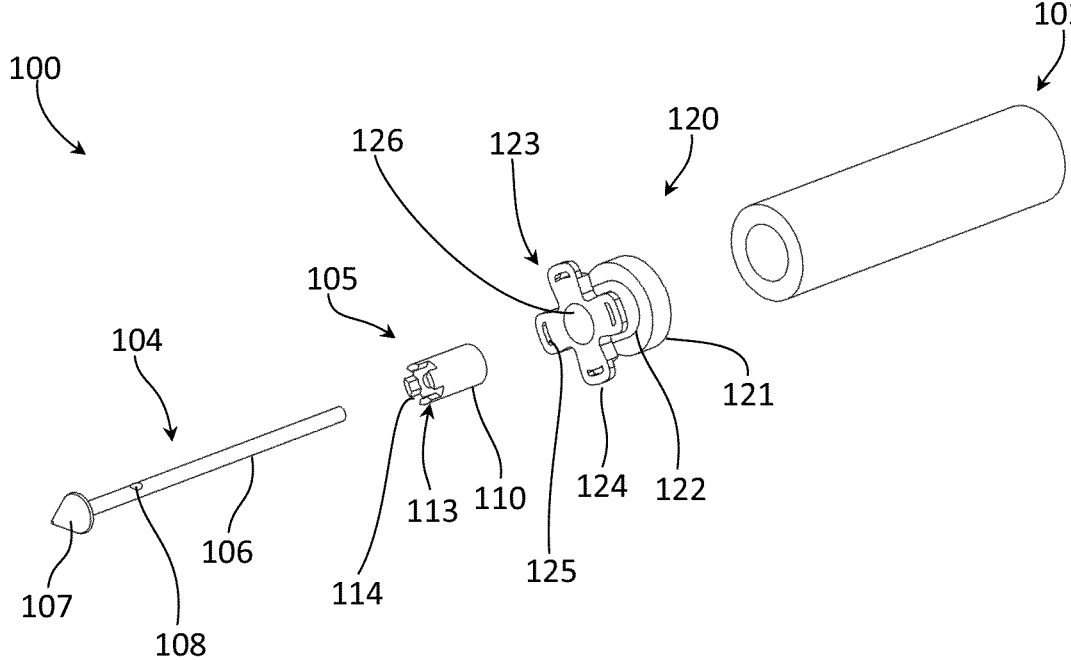
FIG. 13 is an exploded perspective view of an alternative applicator along with a tube in its manufactured configuration, in which case the tube mechanically engages the retainer before deployment.

Referring to FIG. 13 a placement device 100 comprises a stem 102 and a needle 104 with a stem 106, a tip 107, and retainer snap fit dimples 108 on the stem. A retainer 105 comprises a base 110 and a castellated distal end 113 with four axially-extending fingers 114. In other embodiments however there may be a different number of fingers. A tube 120 is shown, for clarity, in FIG. 13 with its distal flange extending laterally, even though it is supplied with the flange near axial on the retainer 105. The tube 120 comprises:

a proximal flange 121;

a shank or bridge 122;

a distal flange 123, with four equally-spaced wings 124 each having an outer eyelet 125; and a lumen 126 through the bridge and the flanges.

Figure 14:
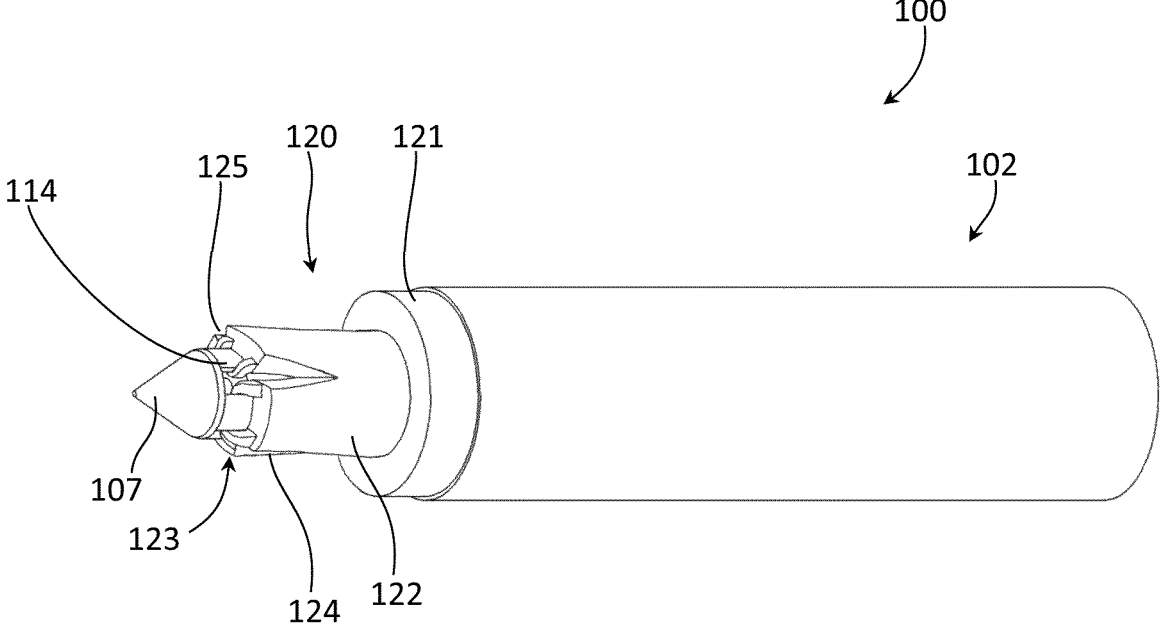
FIG. 14 is a perspective view showing the applicator of FIG. 13 before deployment and FIG. 15 is perspective view of the applicator in use with the needle being retracted causing in situ changing of the shape of the tube from a configuration with a distal flange being near axial to being radial to fully engage behind the tympanic membrane.
Figure 15:
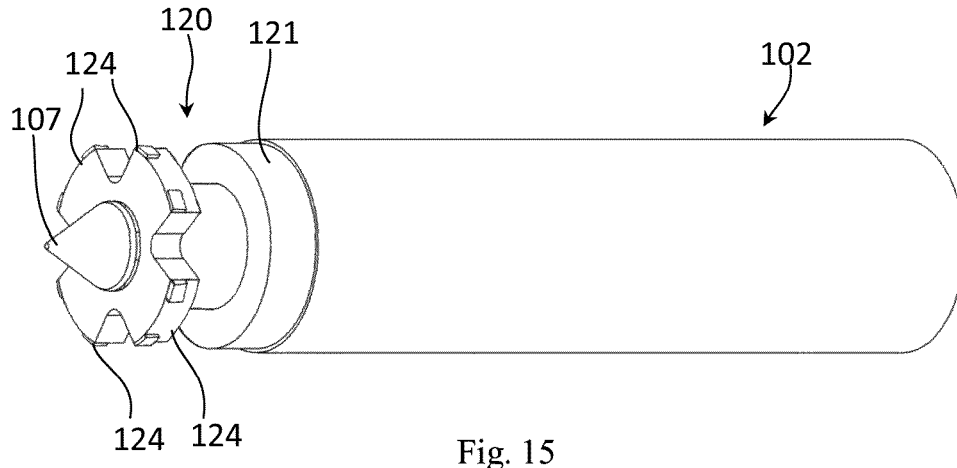

As shown in FIGS. 14 and 15, in this case the tube 120 distal flange 123 is pulled radially inwardly into the axial position to be retained by mechanical engagement with the retainer 105. In this case the mechanical engagement is achieved by the four eyelets 125 being engaged with the retainer fingers 114, each finger 114 extruding axially through an eyelet 125. The eyelets 125 have a degree of flexibility so that they can extend radially inwardly to engage the fingers 114, as shown in FIG. 14. The materials of the eyelets 125 are of an elastic material to extend over the fingers for assembly.

As the needle tip 107 is pulled through, it causes the eyelets 125 to shear during the retraction of the needle into the cartridge. The remainder of the tube is of a tougher material and thus the elastic material of the tube's eyelets 125 is sheared. This sheared material will be retracted into the cartridge under the needle tip. This provides the configuration shown in FIG. 15, the tube being deployed with a distal flange having four wings 124.

Figure 16:
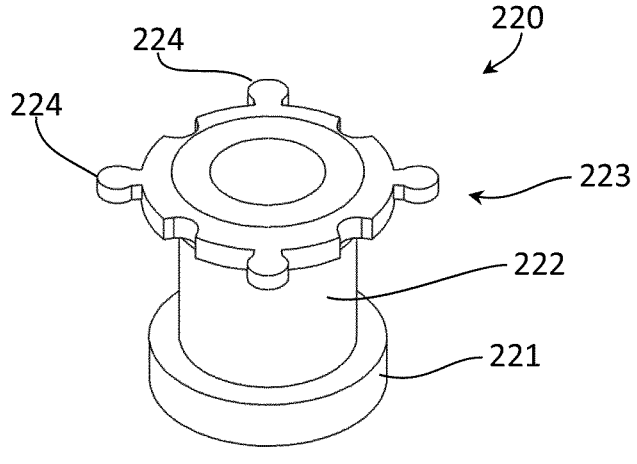
FIG. 16 is a perspective view of an alternative tube in its deployed configuration, this tube having an alternative arrangement for mechanically engaging the retainer before deployment.

It is envisaged that different forms of mechanical locking or engagement may be employed. For example, FIG. 16 shows a tube 220 having:

a proximal flange 221;

a shank 222; and a distal flange 223 with tabs 224 having a neck and a head which engage with a corresponding female feature of the retainer.

Figure 17:
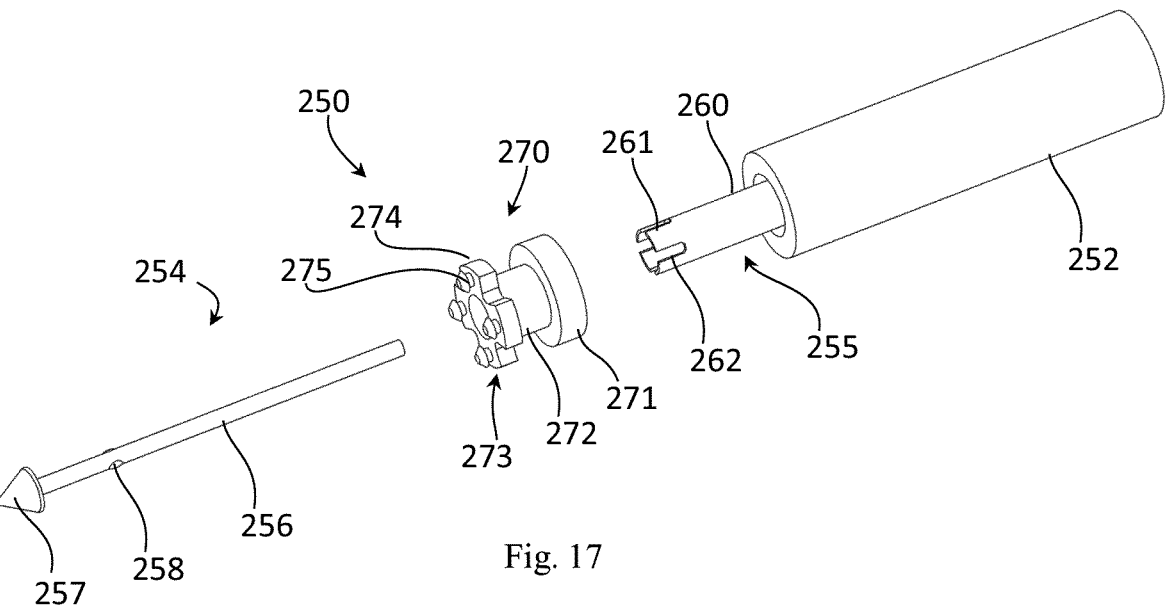
FIG. 17 is a perspective view showing an applicator and a tube in its as-manufactured configuration, in which case there is a further alternative arrangement for mechanical engagement of the tube distal flange with the retainer.
Figure 18:
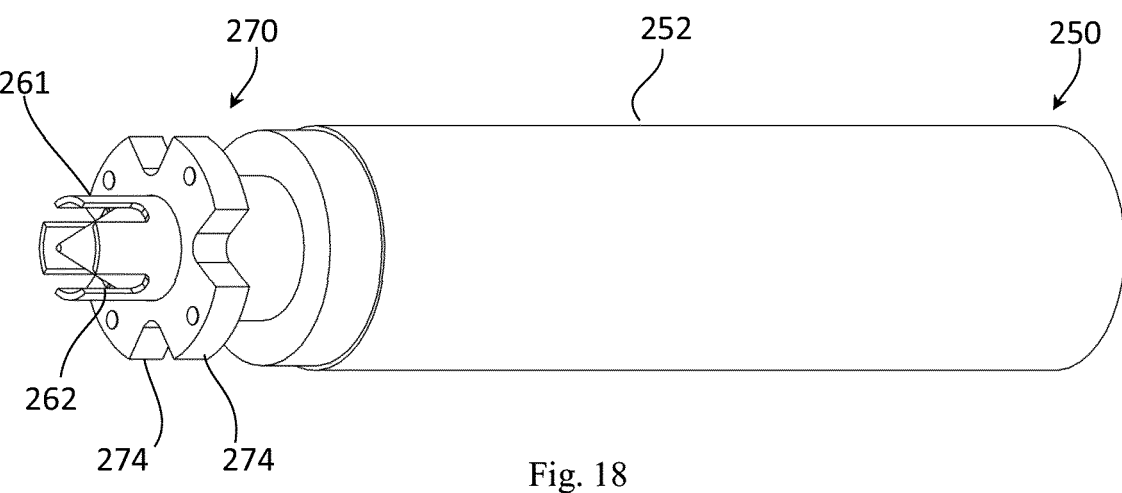
FIG. 18 shows the applicator with the tube in its final configuration with mechanical tabs removed

Referring to FIGS. 17 and 18 an alternative placement device 250 has a stem 252, and a needle 254 with a stem 256, a tip 257, and retainer snap-fit dimples 258. A retainer 255 in this case comprises a main cylindrical body 260 and axially-directed fingers 261 defining axial slots 262 between them. A tube 270, shown in FIG. 17 in its as-manufactured configuration, has a proximal flange 271, a bridge or shank 272, and a distal flange 273 with flanges 274 having tabs 275. The tabs 275 have heads for engaging behind the slots 262 when the wings 274 are axially, the tabs 275 extending radially inwardly. FIG. 18 shows the tube 270 after deployment, when the retainer fingers 261 (still shown here in the distal position) have been pulled proximally to shear the tabs 275 from the wings 274.

In other embodiments, the distal flange is temporarily attached to the retainer by way of welding. For example, referring to FIG. 19 a placement device cartridge 300 has a stem 302 and a needle with a retainer 305 and a tip 307. A tympanostomy tube 320 is attached to the retainer 305 to have the same configuration as in other embodiments. However, in this case the attachment is by way of welding. The tube 320 comprises a proximal flange 321, a bridge 322, and a distal flange 323 formed by four wings 324. Each wing 324 has a spot weld 326 to temporarily affix it to the retainer 305, until they are detached by the needle tip 307 being pulled through as in some of the other embodiments.

Figure 19:
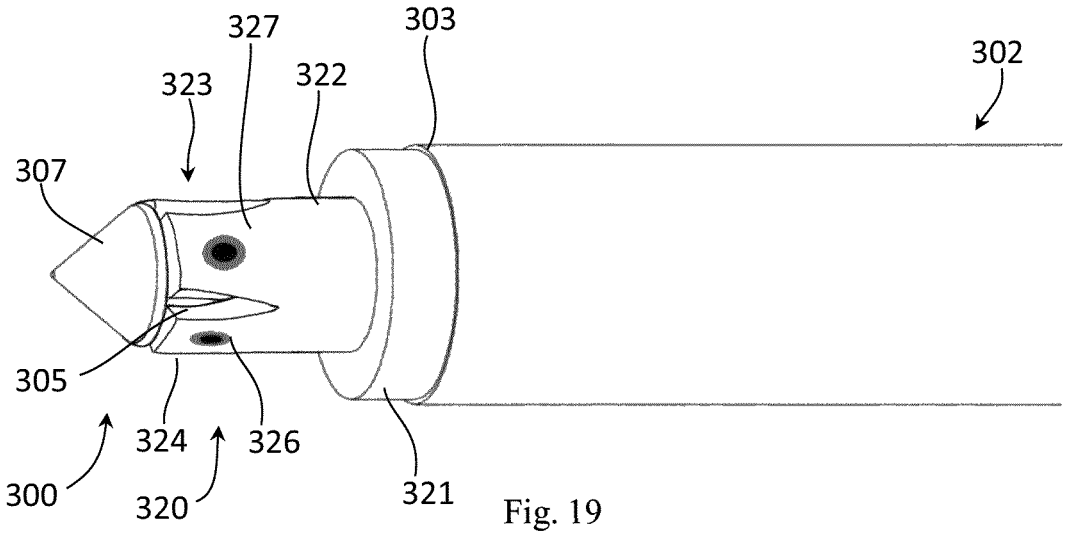
FIG. 19 is a perspective view of the distal end of an alternative applicator of the invention in this case involving welding.
Figure 20:
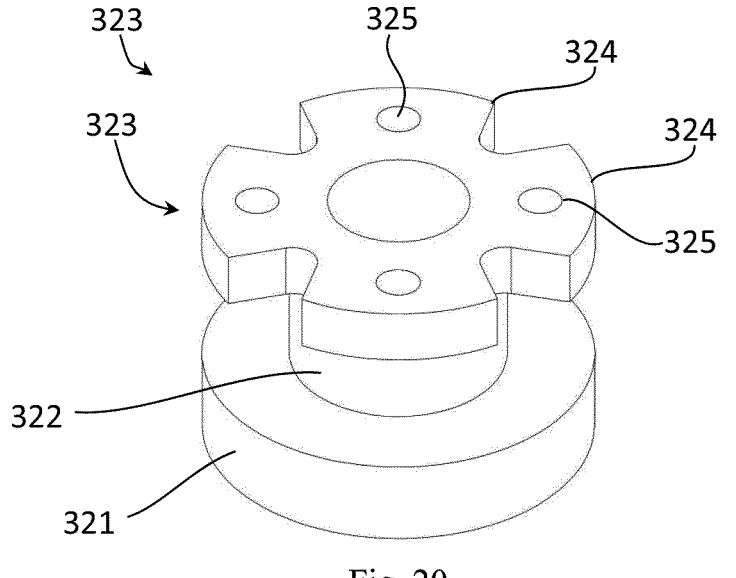
FIG. 20 is a perspective view of a tube in its as-manufactured shape, with holes in distal flange wings for magnetic inserts or inserts for welding material.

FIG. 20 shows the tube 320 of FIG. 19 as manufactured, with an aperture 325 for insertion of material which is more susceptible to welding. In other embodiments this may be for insertion of material which is magnetic. Of course, insertion of the material is preferably done during manufacture.

The spot weld may be performed on a chosen part of the wing 324, the wings each being of an homogenous construction. Alternatively, some or all wings may have a discrete portion suitable for welding by having different characteristics, such as for example having an insert of a different material which is more suitable for welding and/or being of a different thickness. The welding may for example be ultrasonic. Where there are inserts, they may be of a metalized material or plastics material and the welding may be laser or ultrasonic welding.

Figure 21:
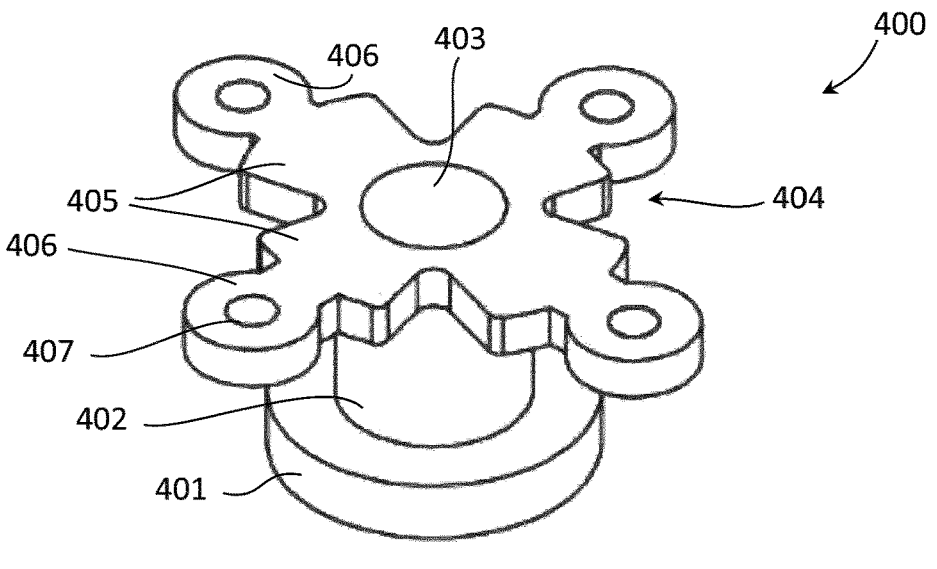
FIGS. 21 and 22 are a perspective view and a longitudinal sectional view of an alternative tube.
Figure 22:
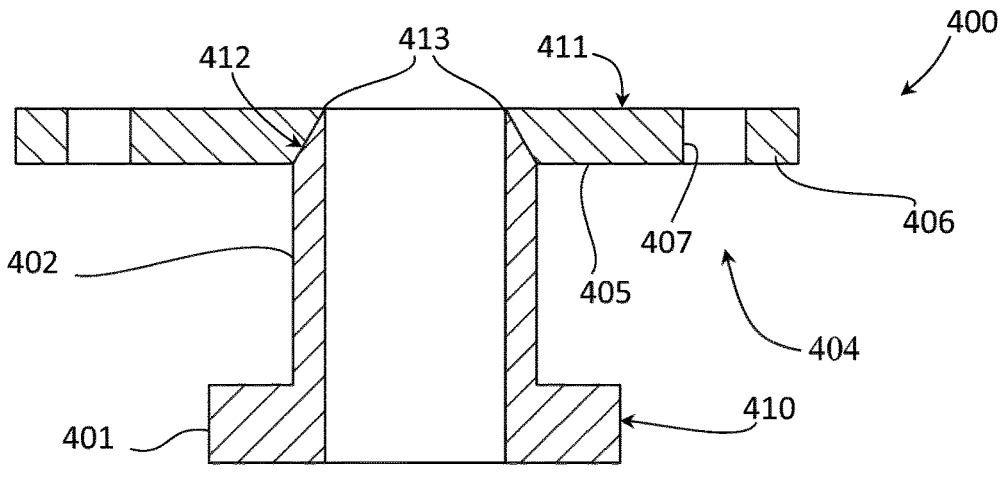

Referring to FIGS. 21 and 22 a tube 400 has a proximal flange 401, a bridge or shank 402 with a lumen 403, and a distal flange 404. The latter comprises a set of four tabs at 900 separations, and at the radial end of each tab 405 there is an eyelet 406 with an aperture 407 which engages a needle, The tube 400 is two-part, having a Titanium part 410 providing the proximal flange and the bridge, and a flexible and resilient plastics part 411 providing the distal flange. The distal end of the Titanium part 410 comprises a bevel 412 having a distal edge 413 to which the distal flange 404 is over-moulded.

Figure 23:
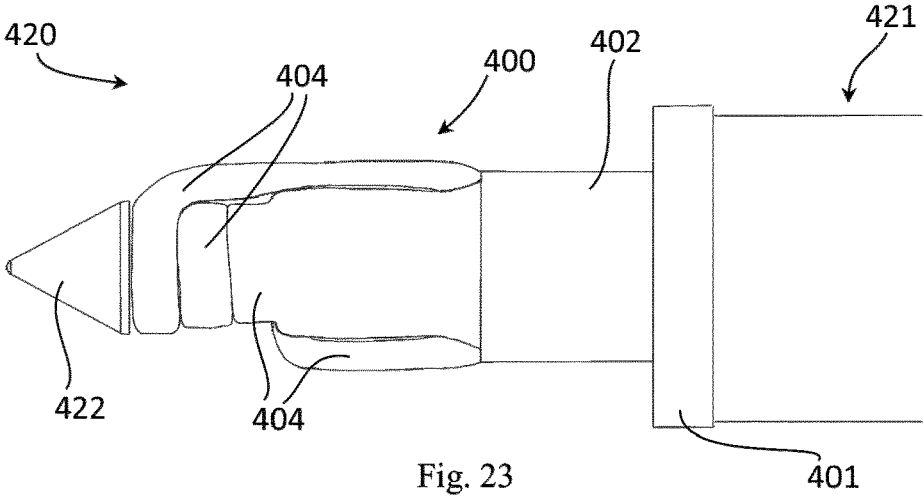
FIG. 23 is a side view showing the tube assembled as part of an applicator before

The distal end of a placement device 420 is shown in FIG. 23, in which the eyelets 406 engage the needle stem behind (proximally of) the tip. The four eyelets 406 form a four-layer sandwich between the needle tip 422 and the edge 413 of the bridge. The different axial distances are possible because the material of the plastics part 411 is resilient. However, it is envisaged that in other embodiments the distal flange tabs may be of different lengths, the longest one engaging the stem at the furthest location distally.

As the needle is withdrawn the four layers (made up of the distal tabs 405 and 406) are squeezed and cut by the rear edge of the needle tip 422 and the edge 413.

The final configuration of the tube 400 is shown in FIG. 24, as the needle 422 is retracted further. Advantageously, the sheared eyelets are fully engaged with the needle stem and so there is no risk that they will remain in situ after surgery.

In other embodiments the distal flange may have wings with metallic inserts for magnetic attachment to the needle and/or retainer. The retainer would be made from a magnetised metal so that the magnets on the flange of the tube would attach to it.

The invention is not limited to the embodiments described but may be varied in construction and detail. For example, the needle may have a lumen, thereby allowing delivery of fluids for aspiration.

The placement device may be arranged so that the tube separates by rotation of the needle rather than pull-through. In this case the wings are not adhered into sockets, rather to a retainer/needle surface which is not recessed. The rotation of the needle causes the wings to be detached from the retainer and forming its deployed configuration.

It is not essential that the placement device have a separable handle and cartridge. They may be integrated. In this case, the needle is single-use.

Where there is a pull-through arrangement, this could be achieved by any suitable drive arrangement, such as a push-button drive of the type used for a retractable pen, or a motorised arrangement.

It is also envisaged that the distal flange may be retained mechanically, in an arrangement other than those illustrated. Further examples are a press fit feature, or different mechanical features to lock the wings in place.

Features of embodiments described above may be interchanged across other embodiments as would be appreciated by those skilled in the art. For example the embodiment of FIGS. 13 to 15 may be modified to have a retainer and tube configured with a different number of flange wings and retainer fingers.

Also, the retainer may be of metal material rather than plastics, and it may be integral with the needle stem. Also, it is not essential that there be a snap-fit feature to hold the retainer on the needle stem. Also, the retaining may be performed by any or some of adhesive, mechanical engagement, welding, and magnetism.

The invention claimed is:

1. A tympanostomy tube applicator comprising: a needle with a tip and a stem, and a stem flange on the stem, a retainer positioned coaxially around the needle stem, between the tip and the stem flange, the retainer comprising an axial through-hole, and a tympanostomy tube mounted on the retainer and coaxial therewith, the tube comprising a proximal flange, a bridge with a lumen, and a distal flange, with the needle stem extending coaxially through the lumen of the tube and the through-hole of the retainer, wherein at least part of the retainer is configured to fit within the lumen of the tympanostomy tube, and the retainer is configured to radially constrain the tympanostomy tube distal flange in a folded configuration, the folded configuration having a direction with a primarily axial component such that movement of the needle tip causes the distal flange to release from the retainer to a deployed position having a direction with a primarily radial component, the applicator further comprising an adhesive connecting the distal flange to the retainer, thereby radially constraining the tube distal flange in the folded, pre-deployed configuration.

2. The tympanostomy tube applicator as claimed in claim 1, wherein the needle and the retainer are configured to move axially to cause radial release of the tube distal flange from the retainer.

3. The tympanostomy tube applicator as claimed in claim 1, wherein the distal flange of the tube comprises wings, and the retainer comprises recesses, the recesses configured for radially constraining said wings.

4. The tympanostomy tube applicator of claim 2, wherein the applicator comprises a stop surface configured to stop axial movement of the tube proximal flange, such that the retainer is configured to, during axial movement of the needle and retainer in the proximal direction squeeze the tube against the stop surface to cause the distal flange to release.

5. The tympanostomy tube applicator as claimed in claim 4, wherein the stop surface is on a sleeve into which the needle is inserted, and wherein the sleeve is configured to receive at least part of the retainer when the needle is retracted.

6. The tympanostomy tube applicator as claimed in claim 1, wherein the needle is arranged to move axially to cause release of the tube distal flange from the retainer, and wherein the applicator comprises a stop surface to stop axial movement of the tube proximal flange, such that the retainer squeezes the tube against the stop surface to cause the distal flange to release during axial movement of the needle in the proximal direction; and wherein the retainer is a single discrete component independent of the needle.

7. The tympanostomy tube applicator as claimed in claim 1, wherein the distal flange of the tube comprises one or more eyelets, and the retainer comprises one or more fingers configured to each engage one of the one or more eyelets on the tube distal flange, constraining the distal flange, thereby in the folded, pre-deployed configuration.

8. The tympanostomy tube applicator as claimed in claim 1, wherein the applicator is a cartridge for attachment to a handle with a mechanism for movement of said needle.

9. The tympanostomy tube applicator as claimed in claim 1, wherein the applicator further comprises an integral handle with a mechanism for movement of the needle.

10. A method of deploying a tympanostomy tube across a tympanic membrane, in which: the tube comprises a proximal flange, a bridge, a distal flange, and a lumen, the method is performed with an applicator comprising a needle with a stem, a stem flange, and a tip, and a retainer with an axial through hole mounted around the needle stem, between the tip and the stem flange; the tube is mounted on the retainer with the needle stem through the tube lumen and through the retainer through-hole, and the tube distal flange is radially constrained in a folded configuration by the retainer to have a primarily axial component facing distally; and in which the method comprises steps of piercing the tympanic membrane with the needle tip and locating the needle so that the tube distal flange is distal of the membrane and the tube bridge passes through the membrane, moving the retainer relative to the tube to cause separation of the tube distal flange from the retainer, freeing the distal flange to spring out in an unconstrained radial orientation, wherein the tube distal flange is adhered to the retainer with an adhesive, creating, thereby, an adhesive bond between the distal flange and the retainer.

11. The method of deploying a tympanostomy tube as claimed in claim 10, wherein the needle is moved axially to release the distal flange.

12. The method of deploying a tympanostomy tube as claimed in claim 10, wherein the needle is moved axially to release the distal flange; and wherein the needle movement is in the proximal direction.

13. The method of deploying a tympanostomy tube as claimed in claim 10, wherein the needle is moved rotationally to release the distal flange.

14. The method of deploying a tympanostomy tube as claimed in claim 10, wherein the adhesive bond is broken during a needle withdrawal and/or the movement of the retainer.

15. The method of deploying a tympanostomy tube as claimed in claim 10, wherein the tube distal flange is retained in the folded configuration by mechanical engagement, and the tube distal flange includes parts which mechanically engage the retainer and distal flange retaining parts are sheared upon a retraction of the needle and/or the movement of the retainer.

16. The method as claimed in claim 10, wherein the tube distal flange is retained in the folded configuration by mechanical engagement, and the tube distal flange includes one or more eyelets which mechanically engage the retainer and are sheared upon a retraction of the needle and/or the movement of the retainer.

17. The method of deploying a tympanostomy tube as claimed in claim 10, wherein the tube distal flange further comprises a magnetic member, the retainer is comprised of a ferromagnetic metal, and magnetism between the magnetic member and the retainer constrains the distal flange in the folded configuration.

18. The method of claim 16, wherein the sheared portions of the distal flange are retracted into the retainer under the needle tip.

* * * * *